United States Patent
Prikril et al.

(10) Patent No.: US 11,707,272 B2
(45) Date of Patent: Jul. 25, 2023

(54) PACKAGED ANTIMICROBIAL MEDICAL DEVICE HAVING IMPROVED SHELF LIFE AND METHOD OF PREPARING SAME

(71) Applicant: ETHICON, LLC, San Lorenzo, PR (US)

(72) Inventors: Michael David Prikril, Lawrenceville, NJ (US); Howard L. Scalzo, Jr., Kenilworth, NJ (US); Leon Gisin, Livingston, NJ (US)

(73) Assignee: CILAG GmbH International, Zug (CH)

( * ) Notice: Subject to any disclaimer, the term of this patent is extended or adjusted under 35 U.S.C. 154(b) by 434 days.

(21) Appl. No.: 16/272,671

(22) Filed: Feb. 11, 2019

(65) Prior Publication Data
US 2019/0239875 A1    Aug. 8, 2019

Related U.S. Application Data

(63) Continuation of application No. 13/727,340, filed on Dec. 26, 2012, now Pat. No. 10,245,025.
(Continued)

(51) Int. Cl.
*B65B 55/18* (2006.01)
*A61B 17/06* (2006.01)
(Continued)

(52) U.S. Cl.
CPC ...... *A61B 17/06133* (2013.01); *A61L 17/005* (2013.01); *B65B 55/18* (2013.01);
(Continued)

(58) Field of Classification Search
CPC .......... A61B 2017/00526; A61B 2017/00889; A61B 2017/06142; A61B 17/06133; A61B 17/06166; B65B 55/18; A61L 17/005
(Continued)

(56) References Cited

U.S. PATENT DOCUMENTS 809,725 A    1/1906   Neff
2,917,878 A  12/1959  Carnarius et al.
(Continued)

FOREIGN PATENT DOCUMENTS

AU    5283486 B    2/1987
CA    2185056 A1   3/1997
(Continued)

OTHER PUBLICATIONS

Thomas A. Barbolt, "Chemistry and Safety of Triclosan, and Its Use as an Antimicrobial Coating on Coated VICRYL* Plus Antibacterial Suture (Coated Polyglactin 910 Suture with Triclosan)". Surgical Infections, May 2002, pp. S-45-S53, vol. 3, No. 3, Supplement 1.
(Continued)

*Primary Examiner* — Valentin Neacsu
*Assistant Examiner* — Mary C Hibbert-Copeland

(57) ABSTRACT

A packaged antimicrobial suture. The packaged antimicrobial suture includes an inner package having a source of antimicrobial agent, the source of antimicrobial agent comprising a plurality of patches, each patch having a pair of antimicrobial material reservoirs; at least one suture positioned within the inner package, the at least one suture comprising one or more surfaces; and an outer package having an inner surface, the outer package having the inner package positioned within; wherein the at least one suture, the inner package and the inner surface of the outer package are subjected to time, temperature and pressure conditions sufficient to transfer an effective amount of the antimicrobial agent from the antimicrobial agent source to the at least one suture and the inner package, thereby substantially inhibiting bacterial colonization on the at least one suture and the inner package. A method of making a packaged antimicrobial suture having is also provided.

14 Claims, 3 Drawing Sheets

Related U.S. Application Data

(60) Provisional application No. 61/621,337, filed on Apr. 6, 2012.

(51) Int. Cl.
  *A61L 17/00* (2006.01)
  *A61B 17/00* (2006.01)

(52) U.S. Cl.
  CPC .................. *A61B 17/06166* (2013.01); *A61B 2017/00526* (2013.01); *A61B 2017/00889* (2013.01); *A61B 2017/06142* (2013.01); *A61L 2300/404* (2013.01)

(58) Field of Classification Search
  USPC ........................................................ 53/425
  See application file for complete search history.

(56) References Cited

U.S. PATENT DOCUMENTS

| | | |
|---|---|---|
| 2,947,282 A | 8/1960 | Brown |
| 3,068,864 A | 12/1962 | Tietze |
| 3,202,273 A | 8/1965 | Riall |
| 3,613,879 A | 10/1971 | Kemble |
| 3,629,477 A | 12/1971 | Model et al. |
| 3,630,348 A | 12/1971 | Benson et al. |
| 3,642,003 A | 2/1972 | Kurtz |
| 3,726,057 A | 4/1973 | Kemble |
| 3,767,362 A | 10/1973 | Griffin et al. |
| 3,815,315 A | 6/1974 | Glick |
| 3,839,297 A | 10/1974 | Wasserman et al. |
| 3,862,304 A | 1/1975 | Kurtz |
| 3,896,812 A | 7/1975 | Kurtz |
| 3,923,154 A | 12/1975 | Tulis et al. |
| 3,939,971 A | 2/1976 | Tulis |
| 3,991,766 A | 11/1976 | Schmitt et al. |
| 4,024,871 A | 5/1977 | Stephenson |
| 4,027,676 A | 6/1977 | Mattei |
| 4,105,034 A | 8/1978 | Shalaby et al. |
| 4,120,395 A | 10/1978 | Mandel et al. |
| 4,126,221 A | 11/1978 | Cerwin |
| 4,185,637 A | 1/1980 | Mattei |
| 4,201,216 A | 5/1980 | Mattei |
| 4,230,663 A | 10/1980 | Forstrom et al. |
| 4,476,590 A | 10/1984 | Scales et al. |
| 4,482,053 A | 11/1984 | Alpern et al. |
| 4,603,538 A | 8/1986 | Shave |
| 4,605,564 A | 8/1986 | Kulla et al. |
| 4,615,705 A | 10/1986 | Scales et al. |
| 4,728,323 A | 3/1988 | Matson |
| 4,846,844 A | 7/1989 | De Leon et al. |
| 4,853,978 A | 8/1989 | Stockum |
| 4,856,504 A | 8/1989 | Yamamoto et al. |
| 4,946,043 A | 8/1990 | Roshdy et al. |
| 4,952,419 A | 8/1990 | De Leon et al. |
| 4,967,902 A | 11/1990 | Sobel et al. |
| 5,019,096 A | 5/1991 | Fox, Jr. et al. |
| 5,037,429 A | 8/1991 | Hermes et al. |
| 5,052,551 A | 10/1991 | Cerwin et al. |
| 5,066,328 A | 11/1991 | Zlotnik |
| 5,091,442 A | 2/1992 | Milner |
| 5,128,101 A | 7/1992 | Boynton |
| 5,131,534 A | 7/1992 | Brown et al. |
| 5,154,283 A | 10/1992 | Brown |
| 5,165,913 A | 11/1992 | Hill et al. |
| 5,180,605 A | 1/1993 | Milner |
| 5,213,210 A | 5/1993 | Cascio et al. |
| 5,222,978 A | 6/1993 | Kaplan et al. |
| 5,230,424 A | 7/1993 | Alpern et al. |
| 5,261,421 A | 11/1993 | Milner |
| 5,284,240 A | 2/1994 | Alpern et al. |
| 5,295,979 A | 3/1994 | Delaurentis et al. |
| 5,359,831 A | 11/1994 | Brown et al. |
| 5,366,081 A | 11/1994 | Kaplan et al. |
| 5,464,580 A | 11/1995 | Popescu et al. |
| 5,468,252 A | 11/1995 | Kaplan et al. |
| 5,468,562 A | 11/1995 | Farivar et al. |
| 5,474,797 A | 12/1995 | Sioshansi et al. |
| 5,518,730 A | 5/1996 | Fuisz |
| 5,529,175 A | 6/1996 | Brunken |
| 5,530,424 A | 6/1996 | Harrison et al. |
| 5,534,288 A | 7/1996 | Gruskin et al. |
| 5,555,976 A | 9/1996 | Pernot |
| 5,556,699 A | 9/1996 | Niira et al. |
| 5,562,211 A | 10/1996 | Simons et al. |
| 5,607,681 A | 3/1997 | Galley et al. |
| 5,623,810 A | 4/1997 | Dey et al. |
| 5,628,395 A | 5/1997 | Daniele et al. |
| 5,708,023 A | 1/1998 | Modak et al. |
| 5,722,992 A | 3/1998 | Goldmann |
| 5,756,145 A | 5/1998 | Darouiche |
| 5,772,640 A | 6/1998 | Modak et al. |
| 5,804,628 A | 9/1998 | Busnel et al. |
| 5,853,745 A | 12/1998 | Darouiche |
| 5,868,244 A | 2/1999 | Ivanov et al. |
| 5,889,075 A | 3/1999 | Roby et al. |
| 5,902,283 A | 5/1999 | Darouiche et al. |
| 5,906,273 A | 5/1999 | Pohle et al. |
| 5,906,825 A | 5/1999 | Seabrook, Jr. et al. |
| 5,945,153 A | 8/1999 | Dearnaley |
| 5,965,610 A | 10/1999 | Modak et al. |
| 5,968,207 A | 10/1999 | Li |
| 5,972,008 A | 10/1999 | Kalinski et al. |
| 5,985,934 A | 11/1999 | Gaffney et al. |
| 5,997,815 A | 12/1999 | Anders et al. |
| 6,021,625 A | 2/2000 | Cerwin et al. |
| 6,034,010 A | 3/2000 | Cartwright et al. |
| 6,037,386 A | 3/2000 | Modak et al. |
| 6,047,815 A | 4/2000 | Cerwin et al. |
| 6,083,208 A | 7/2000 | Modak et al. |
| 6,087,415 A | 7/2000 | Vanderlaan et al. |
| 6,093,414 A | 7/2000 | Capelli |
| 6,106,505 A | 8/2000 | Modak et al. |
| 6,135,272 A | 10/2000 | Sobel et al. |
| 6,165,920 A | 12/2000 | Rubin et al. |
| 6,200,583 B1 | 3/2001 | Sibata et al. |
| 6,224,579 B1 | 5/2001 | Modak et al. |
| 6,238,686 B1 | 5/2001 | Burrell et al. |
| 6,260,699 B1 | 7/2001 | Kaplan et al. |
| 6,315,788 B1 | 11/2001 | Roby |
| 6,420,455 B1 | 7/2002 | Landgrebe et al. |
| 6,475,434 B1 | 11/2002 | Darouiche |
| 6,481,568 B1 | 11/2002 | Cerwin et al. |
| 6,494,898 B1 | 12/2002 | Roby et al. |
| 6,495,100 B1 | 12/2002 | Lin et al. |
| 6,706,024 B2 | 3/2004 | Modak et al. |
| 6,837,027 B2 | 1/2005 | Hickey |
| 6,878,757 B2 | 4/2005 | Roby |
| 6,915,623 B2 | 7/2005 | Dey et al. |
| 6,916,480 B2 | 7/2005 | Anderson et al. |
| 7,070,044 B2 | 7/2006 | Rosenfeld |
| 7,215,401 B2 | 5/2007 | Ishiyama et al. |
| 7,275,640 B2 | 10/2007 | Bourne et al. |
| 7,357,949 B2 | 4/2008 | Trogolo et al. |
| 7,513,093 B2 | 4/2009 | Scalzo et al. |
| 7,651,661 B2 | 1/2010 | Raad et al. |
| 8,069,980 B2 | 12/2011 | Stopek et al. |
| 8,112,973 B2 | 2/2012 | Fischer et al. |
| 8,133,437 B2 | 3/2012 | Scalzo et al. |
| 8,156,718 B2 | 4/2012 | Scalzo et al. |
| 2001/0010016 A1 | 7/2001 | Modak et al. |
| 2001/0016589 A1 | 8/2001 | Modak et al. |
| 2001/0024661 A1 | 9/2001 | Modak et al. |
| 2002/0012760 A1 | 1/2002 | Barry et al. |
| 2002/0055759 A1 | 5/2002 | Shibuya |
| 2003/0108761 A1 | 6/2003 | Eddlemon |
| 2003/0138347 A1 | 7/2003 | Lin |
| 2004/0068293 A1 | 4/2004 | Scalzo et al. |
| 2004/0068294 A1 | 4/2004 | Scalzo et al. |
| 2004/0220614 A1 | 11/2004 | Scalzo et al. |
| 2005/0033251 A1 | 2/2005 | Toreki et al. |
| 2005/0035007 A1 | 2/2005 | Kennedy et al. |
| 2005/0101993 A1 | 5/2005 | Scalzo et al. |
| 2006/0091034 A1 | 5/2006 | Scalzo et al. |

(56) References Cited

U.S. PATENT DOCUMENTS

| | | |
|---|---|---|
| 2006/0091035 A1 | 5/2006 | Scalzo et al. |
| 2006/0231443 A1 | 10/2006 | Jonasson et al. |
| 2007/0010856 A1 | 1/2007 | Cohen |
| 2008/0171972 A1 | 7/2008 | Stopek |
| 2009/0301033 A1 | 12/2009 | Scalzo et al. |
| 2010/0036359 A1 | 2/2010 | Stopek et al. |
| 2010/0078336 A1 | 4/2010 | Reyhan et al. |
| 2010/0116694 A1 | 5/2010 | Stopek et al. |
| 2010/0163435 A1* | 7/2010 | Fischer .............. A61L 17/005 206/204 |
| 2012/0199502 A1 | 8/2012 | Scalzo et al. |
| 2012/0227360 A1 | 9/2012 | Scalzo et al. |
| 2012/0267263 A1 | 10/2012 | Fischer et al. |
| 2013/0193008 A1 | 8/2013 | Reyhan et al. |
| 2013/0193009 A1 | 8/2013 | Scalzo et al. |
| 2013/0264226 A1 | 10/2013 | Prikril et al. |

FOREIGN PATENT DOCUMENTS

| | | |
|---|---|---|
| CA | 2500851 A1 | 4/2004 |
| CA | 2500852 A1 | 4/2004 |
| CN | 2115083 U | 9/1992 |
| CN | 2190968 Y | 3/1995 |
| CN | 1125622 A | 7/1996 |
| CN | 1348346 A | 5/2002 |
| CN | 1713854 A | 12/2005 |
| CN | 201227334 Y | 4/2009 |
| EP | 0470443 A2 | 2/1992 |
| EP | 0471441 A1 | 2/1992 |
| EP | 0761243 A1 | 3/1997 |
| EP | 1159972 A2 | 12/2001 |
| GB | 809725 A | 3/1959 |
| JP | S49-111794 A | 10/1974 |
| JP | H0667376 U | 9/1994 |
| JP | H08-164190 A | 6/1996 |
| JP | H10-504756 A | 5/1998 |
| JP | H11-500330 A | 1/1999 |
| JP | H11-128320 A | 5/1999 |
| JP | 2000507842 A | 6/2000 |
| JP | 2000-190921 A | 7/2000 |
| JP | 2000-237289 A | 9/2000 |
| JP | 2002-9616 A | 1/2002 |
| JP | 2003-512096 A | 4/2003 |
| JP | 2006501975 A | 1/2006 |
| JP | 2006-517808 A | 8/2006 |
| JP | 04-244147 B2 | 3/2009 |
| JP | 10-024040 A | 2/2010 |
| SU | 1438740 A1 | 11/1988 |
| TW | 408011 B | 10/2000 |
| TW | 446822 B | 7/2001 |
| WO | 9622114 A1 | 7/1996 |
| WO | 9639200 A1 | 12/1996 |
| WO | 97/14447 A1 | 4/1997 |
| WO | 9809667 A1 | 3/1998 |
| WO | 0033778 A1 | 6/2000 |
| WO | 0044414 A1 | 8/2000 |
| WO | 0078854 A1 | 12/2000 |
| WO | 0128601 A1 | 4/2001 |
| WO | 2004032703 A2 | 4/2004 |
| WO | 2004032704 A2 | 4/2004 |
| WO | 2007038394 A1 | 4/2007 |
| WO | 2008/045338 A2 | 4/2008 |
| WO | 2010117802 A1 | 10/2010 |
| WO | 2011008547 A1 | 1/2011 |

OTHER PUBLICATIONS

Anuzis et al. "Acetate Antimicrobial Threads". LT 4568 B, Oct. 25, 1999, Database ACS on STN, AN 133: 366471. (Abstract).

Josephine J. Braid et al., "The antibacterial activity of triclosan-impregnated storage boxes against *Staphylococcus aureus, Escherichia colil*, Pseudomonas aeruginosa, Bacillus cereus and Shewanella putrefaciens in conditions simulating domestic use" Journal of Antimocrobial Chemotherapy, 2002, pp. 87-94, vol. 49, 2002 The British Society for Antimicrobial Chemotherapy.

International Search Report & Written Opinion of the International Searching Authority issued in International Application No. PCT/US2010/040405 dated Nov. 4, 2010.

H. N. Bhargava et al., "Triclosan: Applications and safety", American Journal of Infection Control Jun. 1996, pp. 209-218, vol. 24, No. 3.

International Search Report & Written Opinion of the International Searching Authority issued in International Application No. PCT/US2010/029233 dated Jul. 12, 2010.

U.S. Appl. No. 60/416,114, filed Oct. 4, 2002.

U.S. Appl. No. 61/621,337, filed Apr. 6, 2012.

Patent Examination Report No. 3 for related Australian Application No. 2010234778, dated Jul. 30, 2015, 8 pages.

Office Action for related Canadian Application No. 2,766,789, dated May 20, 2016, 4 pages.

Translation of Search Report for related Chinese Application No. 201510870928.X, dated Mar. 23, 2017, 2 pages.

Office Action for related Chinese Application No. 201810622639.1, dated Aug. 24, 2021, 11 pages.

Translation of Search Report for related Chinese Application No. 201810622639.1, dated Jun. 22, 2020, 2 pages.

Office Action for related European Application No. 10 711 810 1-1659, dated Jul. 21, 2017, 5 pages.

Office Action for related Indian Application No. 10385/DELNP/2011, dated Dec. 9, 2018, 5 pages.

Translation of Notification of Reasons for Refusal for related Japanese Application No. 2011-166624, dated Feb. 5, 2013, 2 pages.

Translation of Notification of Reasons for Refusal for related Japanese Application No. 2012-503622, dated Dec. 10, 2013, 4 pages.

Translation of Notice of Preliminary Rejection for related Korean Application No. 10-2011-7025620, dated Nov. 18, 2016, 7 pages.

Translation of Examiner's Decision of Refusal or related Japanese Application No. 2012-503622, dated Oct. 14, 2014.

Office Action for related Canadian Patent Application No. 2,500,851, dated Mar. 16, 2020, 3 pages.

\* cited by examiner

PACKAGED ANTIMICROBIAL MEDICAL DEVICE HAVING IMPROVED SHELF LIFE AND METHOD OF PREPARING SAME

CROSS REFERENCE TO RELATED APPLICATIONS

This application is a continuation of U.S. patent application Ser. No. 13/727,340, filed Dec. 26, 2012, which claims the benefit of U.S. Provisional Application No. 61/621,337 filed Apr. 6, 2012, the contents of which are hereby incorporated by reference in their entirety.

FIELD OF THE INVENTION

The present invention relates to an antimicrobial medical device and an antimicrobial packaged medical device and their methods of making.

BACKGROUND OF THE INVENTION

Each year, patients undergo a vast number of surgical procedures in the United States. Current data shows about twenty-seven million procedures are performed per year. Post-operative or surgical site infections ("SSIs") occur in approximately two to three percent of all cases. This amounts to more than 675,000 SSIs each year.

The occurrence of SSIs is often associated with bacteria that can colonize on implantable medical devices used in surgery. During a surgical procedure, bacteria from the surrounding atmosphere may enter the surgical site and attach to the medical device. Specifically, bacteria can spread by using the implanted medical device as a pathway to surrounding tissue. Such bacterial colonization on the medical device may lead to infection and trauma to the patient. Accordingly, SSIs may significantly increase the cost of treatment to patients.

Implantable medical devices that contain antimicrobial agents applied to or incorporated within have been disclosed and/or exemplified in the art. Examples of such devices are disclosed in European Patent Application No. EP 0 761 243. Actual devices exemplified in the application include French Percuflex catheters. The catheters were dip-coated in a coating bath containing 2,4,4'-tricloro-2-hydroxydiphenyl ether (Ciba Geigy Irgasan (DP300)) and other additives. The catheters then were sterilized with ethylene oxide and stored for thirty days. Catheters coated with such solutions exhibited antimicrobial properties, i.e., they produced a zone of inhibition when placed in a growth medium and challenged with microorganism, for thirty days after being coated. It is not apparent from the application at what temperature the sterilized, coated catheters were stored.

Most implantable medical devices are manufactured, sterilized and contained in packages until opened for use in a surgical procedure. During surgery, the opened package containing the medical device, packaging components contained therein, and the medical device, are exposed to the operating room atmosphere, where bacteria from the air may be introduced. Incorporating antimicrobial properties into the package and/or the packaging components contained therein substantially prevents bacterial colonization on the package and components once the package has been opened. The antimicrobial package and/or packaging components in combination with the incorporation of antimicrobial properties onto the medical device itself would substantially ensure an antimicrobial environment about the sterilized medical device.

SUMMARY OF THE INVENTION

In one aspect, disclosed herein is a packaged antimicrobial suture. The packaged antimicrobial suture includes an inner package having a source of antimicrobial agent, the source of antimicrobial agent comprising a plurality of patches, each patch having a pair of antimicrobial material reservoirs; at least one suture positioned within the inner package, the at least one suture comprising one or more surfaces; and an outer package having an inner surface, the outer package having the inner package positioned within; wherein the at least one suture, the inner package and the inner surface of the outer package are subjected to time, temperature and pressure conditions sufficient to transfer an effective amount of the antimicrobial agent from the antimicrobial agent source to the at least one suture and the inner package, thereby substantially inhibiting bacterial colonization on the at least one suture and the inner package.

In one embodiment, the antimicrobial agent is selected from the group consisting of halogenated hydroxyl ethers, acyloxydiphenyl ethers, and combinations thereof.

In another embodiment, the effective amount of the antimicrobial agent transferred from the source of antimicrobial agent to the suture and the inner package is transferred during an ethylene oxide sterilization process.

In yet another embodiment, the step of subjecting the suture, the inner package and the inner surface of the outer package to conditions sufficient to transfer an effective amount of the antimicrobial agent comprises the steps of placing the outer package having the inner package and the suture therein in a sterilization unit, heating the sterilization unit to a first temperature, adjusting the pressure in the sterilization unit to a first pressure value, injecting steam into the sterilization unit to expose the inner surface of the outer package, the inner package and the suture to water for a first period of time, adjusting the pressure within the sterilization unit to a second pressure value, introducing a chemical sterilization agent into the sterilization unit, maintaining the chemical sterilization agent in the sterilization unit for a second period of time to render a sufficient amount of microorganisms non-viable, removing residual moisture and chemical sterilization agent from the suture, and drying the packaged antimicrobial suture to a desired moisture level.

In still another embodiment, the inner package comprises a containment compartment having an outer cover.

The present invention also relates to a method of making a packaged antimicrobial suture. The method includes the steps of providing an inner package having a source of antimicrobial agent, the source of antimicrobial agent comprising a plurality of patches, each patch having a pair of antimicrobial material reservoirs; positioning at least one suture within the inner package, the at least one suture comprising one or more surfaces; covering the inner package with an outer package having an inner surface; and subjecting the at least one suture, the inner package and the inner surface of the outer package to time, temperature and pressure conditions sufficient to transfer an effective amount of the antimicrobial agent from the antimicrobial agent source to the at least one suture and the inner package, thereby substantially inhibiting bacterial colonization on the at least one suture and the inner package.

BRIEF DESCRIPTION OF THE DRAWINGS

The invention is further explained in the description that follows with reference to the drawings illustrating, by way of non-limiting examples, various embodiments of the invention wherein.

DETAILED DESCRIPTION OF EMBODIMENTS OF THE INVENTION

Figure 1:
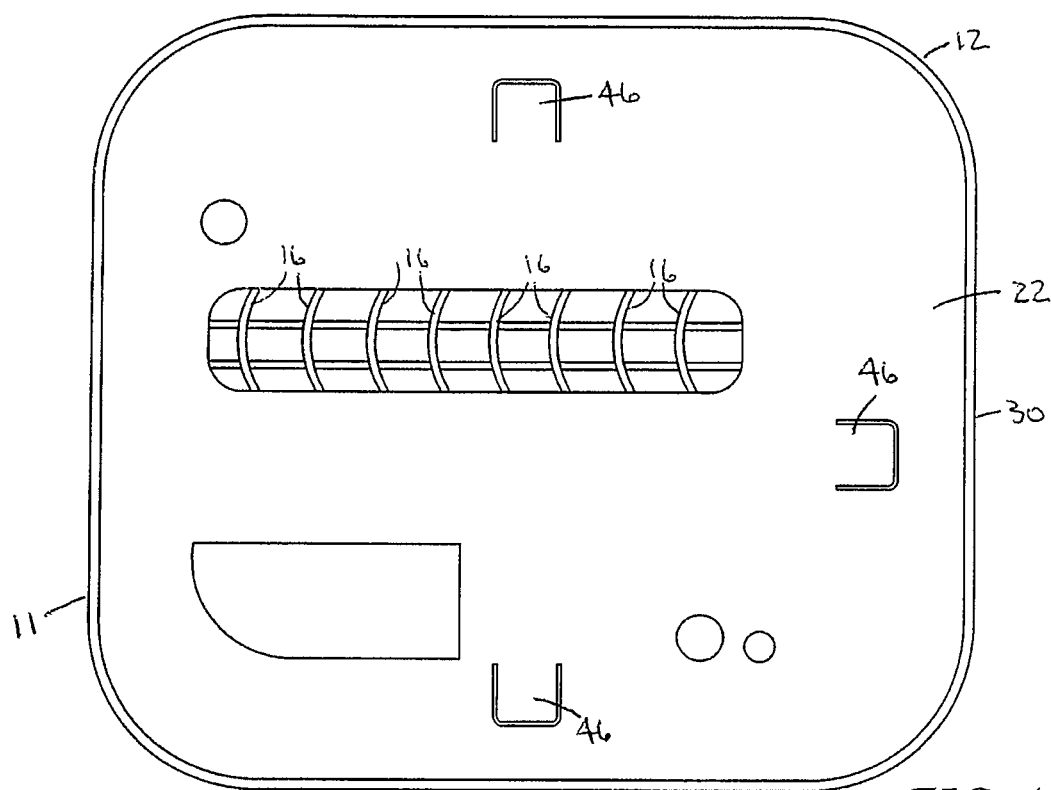
FIG. 1 is a top plan view of one form of a packaged antimicrobial medical device, in accordance herewith, wherein the outer package has been fully removed to reveal a containment compartment.
Figure 2:
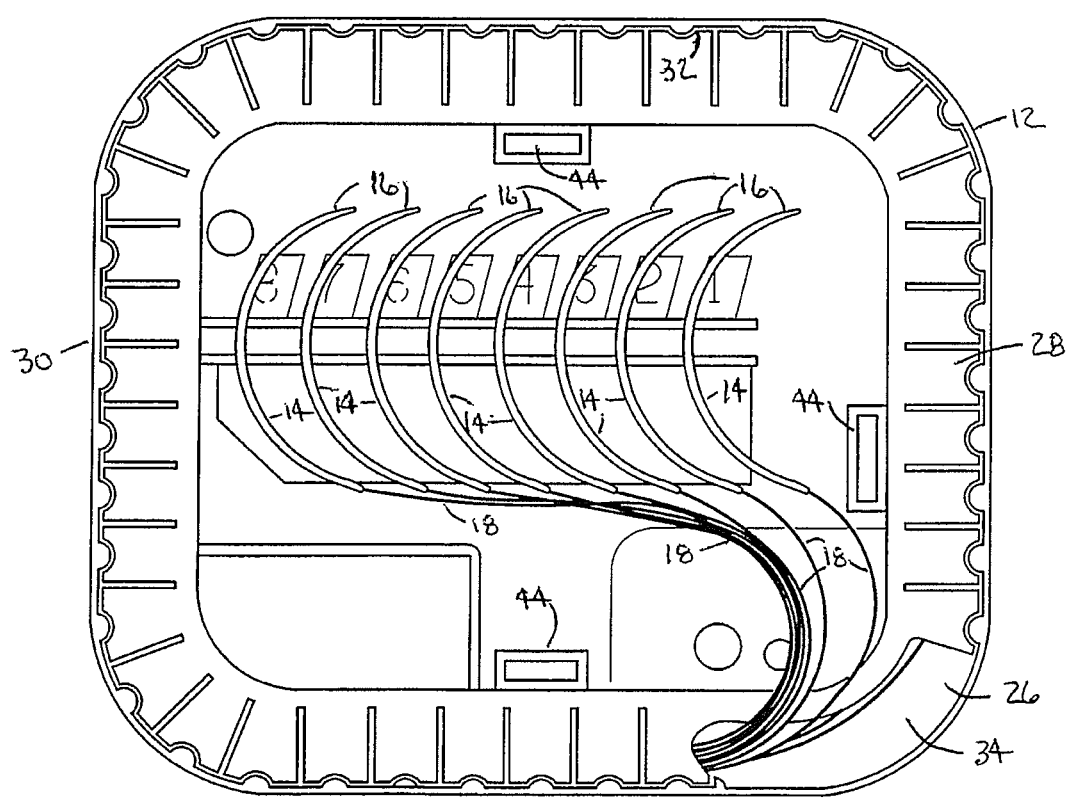
FIG. 2 is a top plan view of the containment compartment of FIG. 1, wherein the outer cover of the containment compartment has been removed to fully expose the base member.

Reference is now made to FIGS. 1-5 wherein like numerals are used to designate like elements throughout.
Packaged Antimicrobial Medical Device Referring now to FIGS. 1-5, one embodiment of a packaged antimicrobial medical device 10 is shown. Packaged antimicrobial medical device 10 includes an inner package 11 having a source of antimicrobial agent. A medical device 14, which may be a needle 16 and suture 18 having one or more surfaces 20 is positioned within the inner package 11. In one embodiment, inner package 11 comprises a containment compartment 12 and an outer cover 22.

As shown, inner surface 24 may be provided with a plurality of patches 54. In one form, each patch has a pair of antimicrobial material reservoirs 56, formed from a material capable of serving as a reservoir. In one form, antimicrobial agent reservoirs 56 may be formed a porous material, such as medical grade paper, or a permeable polymeric film or fabric having a matrix structure. Suitable polymeric materials may include a polyolefin or polyolefin blend, such as polyethylene, polypropylene or blends thereof. In one form, the permeable material comprises TYVEK® nonwoven material, manufactured by E. I. du Pont de Nemours and Company of Wilmington, Del., and made from high-density polyethylene fibers. Advantageously, the antibacterial material can transfer from the patches 54 to the medical device(s) 14 and interior surfaces of the package. In one form, the plurality of patches 54 are positioned about an outer periphery of the inner surface 24 of outer cover 22.

Optionally, the outer cover 22 may have one surface that may be coated with an adsorbent material. In one embodiment, the adsorbent material is effective to adsorb a portion of the antimicrobial agent over time. An outer package 50 having an inner surface 52 is provided to seal the inner package 11 when positioned within.

The containment compartment 12 of packaged antimicrobial medical device 10 includes a base member 26 and a channel cover member 28. Base member 26 includes a top side, bottom side, and an outer periphery 30. As shown, an outer cover 22 may be positioned upon channel cover member 28 and within outer periphery 30, to at least partially enclose medical device 14. The base member 26 may be a substantially flat substantially square member having rounded corners. While in the case of packaged sutures, it may be desired that the base member 26 of packaged antimicrobial medical device 10 be substantially square with rounded corners, other configurations can be used including circular, oval, polygonal, rectangular with rounded corners, and the like and combinations thereof and equivalents thereof. Channel cover 28 includes a top side, bottom side, and periphery 32.

The packaged antimicrobial medical device 10 of the present invention may be assembled in the following manner. Base member 26 is aligned with channel cover member 28 so that rivets 34, if employed are in alignment with the rivet receiving holes 36, and locating pins, if employed, are in alignment with corresponding openings. Also, winding pins 38, if employed, are aligned with corresponding openings 40. Then, channel cover member 28 is then mounted to base member 26 such that rivets, if employed, are inserted into and through corresponding holes and locating pins, if employed, are inserted through corresponding holes. The ends of the rivets 34, if employed, may be spread by using conventional techniques such as heating, ultrasonic treatments, and the like, so that the channel cover member 28 is firmly affixed to the base member 26. In this embodiment, when containment compartment 12 is so formed, a channel 34 is formed, which may advantageously house a wound suture 18.

In one embodiment, outer cover 22 may be provided with a plurality of tabs 46, for positioning within tab receiving members 44, to affix outer cover 22 to base member 26 within outer periphery 30, to at least partially enclose medical device 14.

Further details regarding the construction and geometry of the containment compartments and packages formed therefrom are more fully described in U.S. Pat. Nos. 6,047,815; 6,135,272 and 6,915,623, the contents of each are hereby incorporated by reference in their entirety for all that they disclose.

Containment compartment 12 may be manufactured from conventional moldable materials. It is especially preferred to use polyolefin materials such as polyethylene and polypropylene, other thermoplastic materials, and polyester materials such as nylon, and equivalents thereof. In one embodiment, the containment compartment 12 of the present invention may be injection molded, however, they may also be formed by other conventional processes and equivalents thereof, including thermo-forming. If desired, the packages may be manufactured as individual assemblies or components which are then assembled.

The medical devices described herein are generally implantable medical devices and implants, including but not limited to mono and multifilament sutures, surgical meshes such as hernia repair mesh, hernia plugs, brachy seed spacers, suture clips, suture anchors, adhesion prevention meshes and films, and suture knot clips. Also included are implantable medical devices that are absorbable and non-absorbable.

An absorbable polymer is defined herein as a polymer that will degrade and be absorbed by the body over a period of time when exposed to physiological conditions. Absorbable medical devices typically are formed from generally known, conventional absorbable polymers including but not limited to glycolide, lactide, copolymers of glycolide, or mixtures of polymers, such as polydioxanone, polycaprolactone, oxidized regenerated cellulose and equivalents thereof. Preferably, the polymers include polymeric materials selected from the group consisting of greater than about 70% polymerized glycolide, greater than about 70% polymerized lactide, polymerized 1,4-dioxan-2-one, greater than about 70% polypeptide, copolymers of glycolide and lactide, greater than about 70% cellulosics and cellulosic derivatives. Preferably, absorbable medical devices are made from polydioxanone, poliglecaprone, or a glycolide/lactide copolymer. Examples of absorbable medical device include mono and multifilament sutures. The multifilament suture includes sutures wherein a plurality of filaments is formed into a braided structure. Examples of non-absorbable medical devices include mono and multifilament sutures, surgical meshes such as hernia repair mesh, hernia plugs and brachy seed spacers, which may be polymeric or nonpolymeric. Non-absorbable medical devices may be made in whole or in part from polymeric materials that include, but are not limited to, polyolefins such as polypropylene; polyamides such as nylon; chlorinated and/or fluorinated hydrocarbons such as Teflon® material; or polyesters such as Dacron® synthetic polyesters; or from nonpolymeric materials that include, but are not limited to, silks, collagen, stainless steel, titanium, cobalt chromium alloy, nitinol. Preferably, the non-absorbable medical devices are made from nylon or polypropylene.

In one embodiment, the sutures and needles that can be packaged in the packages disclosed herein include conventional surgical needles and conventional bioabsorbable and nonabsorbable surgical sutures and equivalents thereof. The packages of the present invention are useful to package small diameter sutures which were previously difficult to package in tray packages because of removal or hang-up problems upon withdrawal of such suture from the packages.

Suitable antimicrobial agents may be selected from, but are not limited to, halogenated hydroxyl ethers, acyloxydiphenyl ethers, or combinations thereof. In particular, the antimicrobial agent may be a halogenated 2-hydroxy diphenyl ether and/or a halogenated 2-acyloxy diphenyl ether, as described in U.S. Pat. No. 3,629,477, and represented by the following formula:

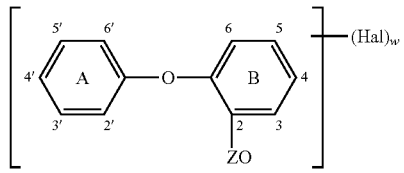

In the above formula, each Hal represents identical or different halogen atoms, Z represents hydrogen or an acyl group, and w represents a positive whole number ranging from 1 to 5, and each of the benzene rings, but preferably ring A can also contain one or several lower alkyl groups which may be halogenated, a lower alkoxy group, the allyl group, the cyano group, the amino group, or lower alkanoyl group. Preferably, methyl or methoxy groups are among the useful lower alkyl and lower alkoxy groups, respectively, as substituents in the benzene rings. A halogenated lower alkyl group, trifluoromethyl group is preferred.

Antimicrobial activity similar to that of the halogen-o-hydroxydiphenyl ethers of the above formula is also attained using the O-acyl derivatives thereof which partially or completely hydrolyze under the conditions for use in practice. The esters of acetic acid, chloroacetic acid, methyl or dimethyl carbamic acid, benzoic acid, chlorobenzoic acid, methylsulfonic acid and chloromethylsulfonic acid are particularly suitable.

One particularly preferred antimicrobial agent within the scope of the above formula is 2,4,4'-trichloro-2'-hydroxydiphenyl ether, commonly referred to as triclosan (manufactured by Ciba Geigy under the trade name Irgasan DP300 or Irgacare MP). Triclosan is a white powdered solid with a slight aromatic/phenolic odor. As may be appreciated, it is a chlorinated aromatic compound which has functional groups representative of both ethers and phenols.

Triclosan is a broad-spectrum antimicrobial agent that has been used in a variety of products, and is effective against a number of organisms commonly associated with SSIs. Such microorganisms include, but are not limited to, genus *Staphylococcus*, *Staphylococcus epidermidis*, *Staphylococcus aureus*, methicillin-resistant *Staphylococcus epidermidis*, methicillin-resistant *Staphylococcus aureus*, and combinations thereof.

In addition to the antimicrobial agents described above, the medical device optionally may have a biocide, a disinfectant and/or an antiseptic, including but not limited to alcohols such as ethanol and isopropanol; aldehydes such as glutaraldehyde and formaldehyde; anilides such as triclorocarbanilide; biguanides such as chlorhexidine; chlorine-releasing agents such as sodium hypochlorite, chlorine dioxide and acidified sodium chlorite; iodine-releasing agents such as povidone-iodine and poloxamer-iodine; metals such as silver nitrate, silver sulfadiazine, other silver agents, copper-8-quinolate and bismuth thiols; peroxygen compounds such as hydrogen peroxide and peracetic acid; phenols; quaternary ammonium compounds such as benzalkonium chloride, cetrimide and ionenes-polyquaternary ammonium compounds. The medical device optionally may have antibiotics, including but not limited to penicillins such as amoxicillin, oxacillin and piperacillin; cephalosporins parenteral such as cefazolin, cefadroxil, cefoxitin, cefprozil, cefotaxime and cefdinir; monobactams such as aztreonam; beta-lactamase inhibitors such as clavulanic acid sulbactam; glycopeptide such as vancomycin; polymixin; quinolones such as nalidixic acid, ciprofloxacin and levaquin; metranidazole; novobiocin; actinomycin; rifampin; aminoglycosides such as neomycin and gentamicin; tetracyclines such as doxycycline; chloramphenicol; macrolide such as erythromycin; clindamycin; sulfonamide such as sulfadiazine; trimethoprim; topical antibiotics; bacitracin; gramicidin; mupirocin; and/or fusidic acid. Optionally, the medical device may have antimicrobial peptides such as defensins, magainin and nisin; lytic bacteriophage; surfactants; adhesion blockers such as antibodies, oligosaccharides and glycolipids; oligonucleotides such as antisense RNA; efflux pump inhibitors; photosensitive dyes such as porphyrins; immune modulators such as growth factors, interleukins, interferons and synthetic antigens; and/or chelators such as EDTA, sodium hexametaphosphate, lactoferrin and transferrin.

Figure 3:
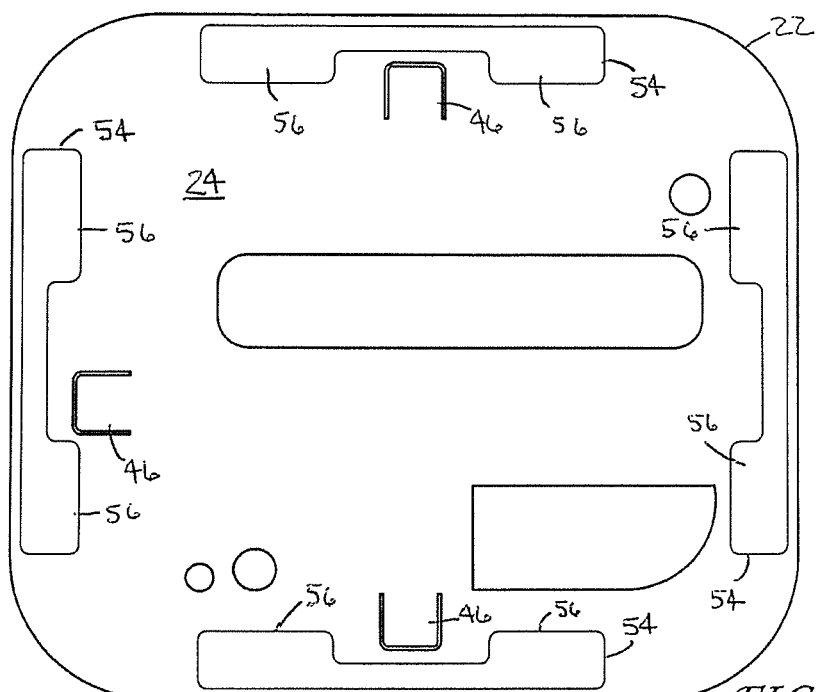
FIG. 3 is a plan view of the underside of the outer cover of the containment compartment, showing a plurality of antimicrobial agent reservoirs disposed about the periphery of the cover.
Figure 4:
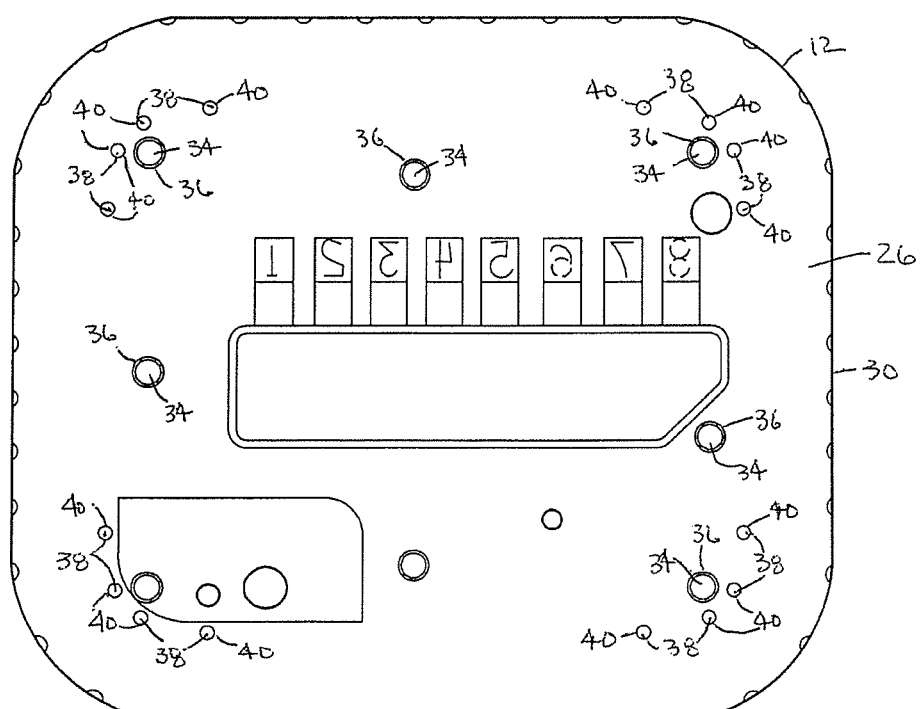
FIG. 4 is a bottom plan view of the containment compartment of the packaged antimicrobial medical device of FIG. 1.
Figure 5:
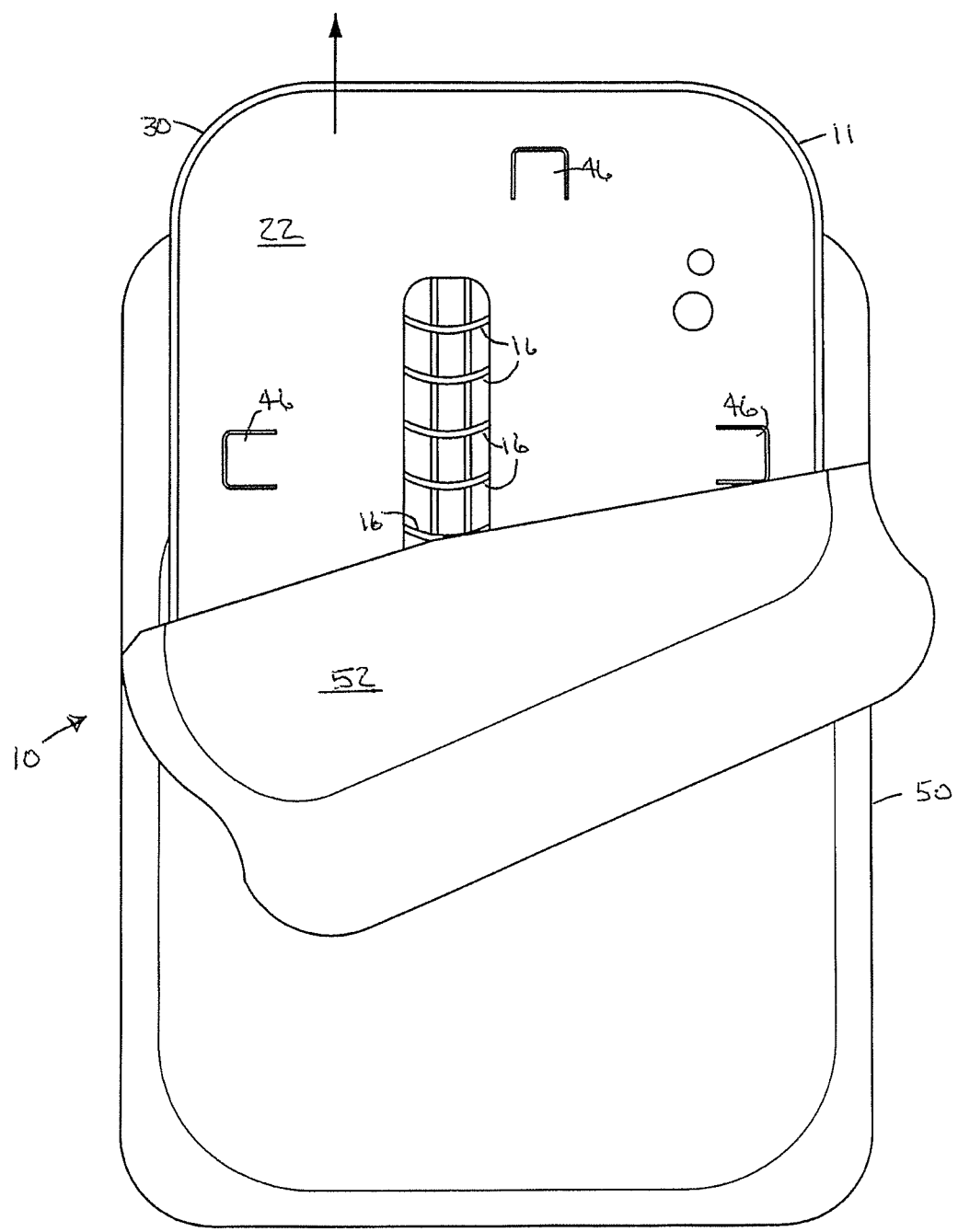
FIG. 5 is a top plan view of the packaged antimicrobial medical device of FIG. 1, wherein the outer package has been partially removed to reveal a portion of the containment compartment.

As shown in FIG. 3, the antimicrobial agent may be delivered to the medical device from a plurality of antimicrobial agent reservoirs 56, attached to the inner surface of outer cover 22. Specifically, the antimicrobial agent is transferred from the antimicrobial agent reservoirs to the medical device when the package, the antimicrobial agent reservoirs and the medical device are subjected to time, temperature and pressure conditions, as described below. For example, the antimicrobial agent reservoirs may be antimicrobial agent-loaded paper reservoirs, antimicrobial agent-loaded porous pouch reservoirs, antimicrobial agent-loaded plastic reservoirs, antimicrobial agent-loaded sponge or foam reservoirs, an antimicrobial agent-loaded tape or patch. As indicated above, in one form, the plurality of antimicrobial agent reservoirs 56 may be a series of TYVEK® patches 54.

As indicated, the packaged antimicrobial medical devices disclosed herein utilize an adsorbent or absorbent material to improve shelf life over packaged antimicrobial sutures that do not utilize an adsorbent or absorbent material. It has been shown that the shelf life of an antimicrobial medical device, such as a triclosan-containing suture, is believed to be limited by triclosan levels that increase over time during normal and accelerated storage conditions. It has been surprisingly discovered that certain adsorbent or absorbent materials may serve as a buffering agent to moderate the rate of increase of triclosan on the medical device.

In one embodiment, an adsorbent or absorbent material is provided by coating the adsorbent or absorbent material on at least a portion of one surface of the inner package, 11. In another embodiment, the adsorbent or absorbent material is provided by placing an adsorbent or absorbent substrate (not shown) within the outer package. In another embodiment, the adsorbent or absorbent substrate is formed by coating a substrate with an adsorbent or absorbent material. In yet another embodiment, the adsorbent or absorbent substrate is formed of an adsorbent or absorbent material. In still yet another embodiment, the adsorbent or absorbent material provided on at least a portion of one surface of the inner package, is provided on at least one surface of outer cover 22.

Materials having adsorbent or absorbent properties, include bentonite, activated carbon, activated alumina, silica gel, zeolite, super-absorbant polymers, humectants, polymeric coatings, ground polymeric coatings, natural products, non-paper substrates, and clays, including kaolin. Clays, such as kaolin, have proven to be particularly effective.

Additionally, the medical device may optionally have a coating thereon, and/or may optionally comprise one or more surfaces having an antimicrobial agent disposed thereon prior to any transfer of antimicrobial agent to the medical device from the antimicrobial agent source. For example, it is advantageous to apply a coating composition having an antimicrobial agent therein to the surface of the medical device. Examples of medical devices, as well as coatings that may be applied thereto, may be found in U.S. Pat. Nos. 4,201,216, 4,027,676, 4,105,034, 4,126,221, 4,185,637, 3,839,297, 6,260,699, 5,230,424, 5,555,976, 5,868,244, and 5,972,008, each of which is hereby incorporated herein in its entirety. As disclosed in U.S. Pat. No. 4,201,216, the coating composition may include a film-forming polymer and a substantially water-insoluble salt of a $C_6$ or higher fatty acid. As another example, an absorbable coating composition that may be used for an absorbable medical device may include poly(alkylene oxylates) wherein the alkylene moieties are derived from $C_6$ or mixtures of $C_4$ to $C_{12}$ diols, which is applied to a medical device from a solvent solution, as disclosed in U.S. Pat. No. 4,105,034. The coating compositions may include a polymer or copolymer, which may include lactide and glycolide, as a binding agent. The coating compositions may also include calcium stearate, as a lubricant; and an antimicrobial agent. The coating may be applied to the device by solvent-based coating techniques, such as dip coating, spray coating, or suspended drop coating, or any other coating means.

Absorbable medical devices are moisture sensitive, that is, they are devices that will degrade if exposed to moisture in the atmosphere or in the body. It is known by those of ordinary skill in the art that medical devices made from absorbable polymers may deteriorate and lose their strength if they come into contact with water vapor prior to use during surgery. For instance, the desirable property of in vivo tensile strength retention for sutures will be rapidly lost if the sutures are exposed to moisture for any significant period of time prior to use. Therefore, it is desirable to use a hermetically sealed package for absorbable medical devices. A hermetically sealed package is defined herein to mean a package made of a material that serves as both a sterile barrier and a gas barrier, i.e., prevents or substantially inhibits moisture and gas permeation.

Referring again to FIG. 5, materials useful for constructing outer packages 50 may include, for example, include single and multilayered conventional metal foil products, often referred to as heat-sealable foils. These types of foil products are disclosed in U.S. Pat. No. 3,815,315, which is hereby incorporated by reference in its entirety. Another type of foil product that may be utilized is a foil laminate referred to in the field of art as a peelable foil. Examples of such peelable foil and substrates are disclosed in U.S. Pat. No. 5,623,810, which is hereby incorporated by reference in its entirety. If desired, conventional non-metallic polymer films in addition to or in lieu of metal foil may be used to form the package for absorbable medical devices. Such films are polymeric and may include conventional polyolefins, polyesters, acrylics, halogenated hydrocarbons and the like, combinations thereof and laminates. These polymeric films substantially inhibit moisture and oxygen permeation and may be coated with conventional coatings, such as, for example, mineral and mineral oxide coatings that decrease or reduce gas intrusion. The package may comprise a combination of polymer and metal foils, particularly a multi-layer polymer/metal-foil composite, such as a polyester/aluminum foil/ethylacrylic acid laminate.

Nonabsorbable medical devices may be packaged in any of the materials described above. In addition, it is desirable to package nonabsorbable medical devices in a package made of a material that serves as a sterile barrier, such as a porous material, i.e., medical grade paper, or a polymeric film or fabric that is permeable to moisture and gas, i.e., TYVEK® nonwoven material, manufactured by E. I. du Pont de Nemours and Company of Wilmington, Del., and made from high-density polyethylene fibers. Preferably, nonabsorbable medical devices are packaged in the same packaging materials that are used for absorbable medical devices, such as hermetically sealed packages, when it is desirable to have antimicrobial medical devices having a shelf life of at least 6 months, preferably at least 1 year and most preferably at least 2 years.

Microorganisms of the genus *Staphylococcus* are the most prevalent of all of the organisms associated with device-related surgical site infection. *S. aureus* and *S. epidermidis* are commonly present on patients' skin and as such are introduced easily into wounds. An efficacious antimicrobial agent against *Staphylococcus* is 2,4,4'-trichloro-2'-hydroxydiphenyl ether. This compound has a minimum inhibitory concentration (MIC) against *S. aureus* of 0.01 ppm, as measured in a suitable growth medium and as described by Bhargava, H. et al in the American Journal of Infection Control, June 1996, pages 209-218. The MIC for a particular antimicrobial agent and a particular microorganism is defined as the minimum concentration of that antimicrobial agent that must be present in an otherwise suitable growth medium for that microorganism, in order to render the growth medium unsuitable for that microorganism, i.e., the minimum concentration to inhibit growth of that microorganism. The phrases "an amount sufficient to substantially inhibit bacterial colonization" and "an effective amount" of the antimicrobial agent, as used herein, are defined as the minimum inhibitory concentration for *S. aureus* or greater.

A demonstration of this MIC is seen in the disk diffusion method of susceptibility. A filter paper disk, or other object, impregnated with a particular antimicrobial agent is applied to an agar medium that is inoculated with the test organism. Where the antimicrobial agent diffuses through the medium, and as long as the concentration of the antimicrobial agent is above the minimum inhibitory concentration (MIC), none of the susceptible organism will grow on or around the disk for some distance. This distance is called a zone of inhibition. Assuming the antimicrobial agent has a diffusion rate in the medium, the presence of a zone of inhibition around a disk impregnated with an antimicrobial agent indicates that the organism is inhibited by the presence of the antimicrobial agent in the otherwise satisfactory growth medium. The diameter of the zone of inhibition is inversely proportional to the MIC.

Method for Making an Antimicrobial Medical Device

In accordance with the various methods of the present invention, a method of making a packaged antimicrobial suture is provided. The method includes the steps of providing an inner package having a source of antimicrobial agent, the source of antimicrobial agent comprising a plurality of patches, each patch having a pair of antimicrobial material reservoirs; positioning at least one suture within the inner package, the at least one suture comprising one or more surfaces; covering the inner package with an outer package having an inner surface; and subjecting the at least one suture, the inner package and the inner surface of the outer package to time, temperature and pressure conditions sufficient to transfer an effective amount of the antimicrobial agent from the antimicrobial agent source to the at least one suture and the inner package, thereby substantially inhibiting bacterial colonization on the at least one suture and the inner package.

As will be described in more detail hereinbelow, the step of subjecting the suture, the inner package and the inner surface of the outer package to conditions sufficient to transfer an effective amount of the antimicrobial agent includes the steps of placing the outer package having the inner package and the suture therein in a sterilization unit, heating the sterilization unit to a first temperature, adjusting the pressure in the sterilization unit to a first pressure value, injecting steam into the sterilization unit to expose the inner surface of the outer package, the inner package and the suture to water vapor for a first period of time, adjusting the pressure within the sterilization unit to a second pressure value, introducing a chemical sterilization agent into the sterilization unit, maintaining the chemical sterilization agent in the sterilization unit for a second period of time to render a sufficient amount of microorganisms non-viable, removing residual moisture and chemical sterilization agent from the suture and drying the packaged antimicrobial suture to a desired moisture level. In one embodiment, the step of introducing a chemical sterilization agent comprises introducing ethylene oxide gas into the sterilization unit.

In one embodiment, the medical device is directly exposed to the antimicrobial agent, i.e., the antimicrobial agent source is located in the package having the medical device. For example, the package may contain an antimicrobial agent source, may have an antimicrobial agent source attached to the inner surface of the package, or the antimicrobial agent source may be integral with one or more packaging component in the package or with the package itself. In these embodiments, the medical device is positioned within the package and may initially be free of an antimicrobial agent or may initially comprise one or more surfaces having an antimicrobial agent disposed thereon. As indicated, the package, the antimicrobial agent source and the medical device are then subjected to time, temperature and pressure conditions sufficient to transfer an effective amount of the antimicrobial agent from the antimicrobial agent source to the medical device, thereby substantially inhibiting bacterial colonization on the medical device.

In the case where the medical device is initially free of an antimicrobial agent, the antimicrobial agent is delivered to the medical device from an antimicrobial agent source when the package, the antimicrobial agent source and the medical device are subjected to time, temperature and pressure conditions sufficient to transfer a portion of the antimicrobial agent from the antimicrobial agent source to the medical device.

In the case where the medical device initially comprises one or more surfaces having an antimicrobial agent disposed thereon, the time, temperature and pressure conditions are sufficient to transfer a portion of each of the antimicrobial agent disposed on the medical device and the antimicrobial agent in the antimicrobial agent source to the inner surface of the package, such that an effective amount of the antimicrobial agent is retained on the medical device, thereby substantially inhibiting bacterial colonization on the medical device and the inner surface of the package. In this embodiment, the amount or concentration of antimicrobial agent on the medical device is stabilized by providing additional antimicrobial agent in the packaging environment.

Alternatively, the medical device may be positioned within a package, and the package having the medical device is exposed indirectly to an external antimicrobial agent source, i.e., the antimicrobial agent source is external to the package having the medical device. Specifically, the antimicrobial agent source and the package having the medical device are subjected to time, temperature and pressure conditions sufficient to transfer an effective amount of the antimicrobial agent from the antimicrobial agent source to the medical device within the package, thereby substantially inhibiting bacterial colonization on the medical device. In this embodiment, the package may be made from a material that serves as a sterile barrier, such as a porous material or polymeric film that is permeable to moisture and gas, such that a gaseous antimicrobial agent source is capable of permeating or transmitting as a vapor through the package. For example, the package having the medical device may be placed in a sealed environment, and the antimicrobial agent source may be contained within the sealed environment or may be subsequently introduced to the sealed environment. The antimicrobial agent source may be any vapor form of the antimicrobial agent.

The rate of transfer of an antimicrobial agent such as triclosan from the antimicrobial agent source to the medical device is substantially dependent upon the time, temperature and pressure conditions under which the package and the medical device are processed, stored and handled. The conditions to effectively transfer an antimicrobial agent such as triclosan include a closed environment, atmospheric pressure, a temperature of greater than 40° C., for a period of time ranging from 4 to 8 hours. Also included are any combinations of pressure and temperature to render a partial pressure for the antimicrobial agent that is the same as or greater than the partial pressure rendered under the conditions described above, in combination with a period of time sufficient to render an effective amount or concentration of the antimicrobial agent on the medical device, i.e., the minimum inhibitory concentration (MIC) for $S.$ $aureus$ or greater. Specifically, it is known to one of ordinary skill that if the pressure is reduced, the temperature may be reduced to effect the same partial pressure. Alternatively, if the pressure is reduced, and the temperature is held constant, the time required to render an effective amount or concentration of the antimicrobial agent on the medical device may be shortened. Generally, the amount of antimicrobial agent in the antimicrobial agent source is at least that amount which is necessary to deliver the effective amount of the antimicrobial agent on the medical device, when exposed to the conditions described below.

Medical devices typically are sterilized to render microorganisms located thereon substantially non-viable. In particular, sterile is understood in the field of art to mean a minimum sterility assurance level of $10^{-6}$. Examples of sterilization processes are described in U.S. Pat. Nos. 3,815,315, 3,068,864, 3,767,362, 5,464,580, 5,128,101 and 5,868,244, each of which is incorporated herein in its entirety. Specifically, absorbable medical devices may be sensitive to radiation and heat. Accordingly, it may be desirable to sterilize such devices using conventional sterilant gases or agents, such as, for example, ethylene oxide gas.

An ethylene oxide sterilization process is described below, since the time, temperature and pressure conditions sufficient to transfer the antimicrobial agent from the antimicrobial agent source to the medical device, are present in an ethylene oxide sterilization process. However the time, temperature and pressure conditions sufficient to transfer the antimicrobial agent from the antimicrobial agent source to the medical device, may be effected alone or in other types of sterilization processes, and are not limited to an ethylene oxide sterilization process or to sterilization processes in general.

As discussed above, absorbable medical devices are sensitive to moisture and are therefore often packaged in hermetically sealed packages, such as sealed foil packages. However, sealed foil packages are also impervious to sterilant gas. In order to compensate for this and utilize foil packages in ethylene oxide gas sterilization processes, processes have been developed using foil packages having gas permeable or pervious vents (e.g., TYVEK® nonwoven material, manufactured by E. I. du Pont de Nemours and Company of Wilmington, Del.). The gas permeable vents are mounted to an open end of the package and allow the passage of air, water vapor and ethylene oxide into the interior of the package. After the sterilization process is complete, the package is sealed adjacent to the vent so the vent is effectively excluded from the sealed package, and the vent is cut away or otherwise removed, thereby producing a gas impervious hermetically sealed package. Another type of foil package having a vent is a pouch-type package having a vent mounted adjacent to an end of the package, wherein the vent is sealed to one side of the package creating a vented section. After the sterilization process is complete the package is sealed adjacent to the vented section, and the sealed package is cut away for the vented section.

In one embodiment, the antimicrobial agent source is placed within the package, attached to the inner surface of the package, or is integral with one or more packaging component in the package or with the package itself. After the peripheral seal and side seals have been formed in the package, the packaged medical device may be placed into a conventional ethylene oxide sterilization unit. If the package is a foil package, the antimicrobial agent source may be any of the antimicrobial agent sources described above or the antimicrobial agent source may be an antimicrobial agent loaded-gas permeable vent. For example, an antimicrobial agent such as triclosan may be loaded onto a TYVEK® gas permeable vent by coating the TYVEK® strip with a solution of ethyl acetate and triclosan; the antimicrobial agent loaded gas permeable vent is positioned within a package by mounting it to a hermetic packaging material; the medical device is positioned within the hermetic packaging material; the periphery of the hermetic packaging material is sealed in a manner to enclose the medical device and to allow the passage of gas into the interior of the hermetic packaging material through the vent; the packaging material having the antimicrobial agent loaded gas permeable vent and the medical device is subjected to time, temperature and pressure conditions sufficient to transfer an effective amount of the antimicrobial agent from the antimicrobial agent loaded gas permeable vent to the medical device; the packaging material is sealed to enclose the medical device and exclude the vent; and the vent is cut away to thereby produce an antimicrobial medical device.

In another embodiment, the antimicrobial agent source may be introduced into the sterilization or other unit external to the package having the medical device. For example, the medical device is positioned within the package; the package having the medical device is exposed to an antimicrobial agent source; and the package having the medical device and the antimicrobial agent source is subjected to time, temperature and pressure conditions sufficient to transfer an effective amount of the antimicrobial agent from the antimicrobial agent source to the medical device within the package, thereby substantially inhibiting bacterial colonization on the medical device. The package may be made from a material that serves as a sterile barrier, such as a porous material or a polymeric film that is permeable to moisture and gas, or from a material that results in a hermetically sealed package.

Prior to the start of the cycle, the sterilization unit may be heated to an internal temperature of about 25° C. The sterilization unit is maintained about 22 to 37° C. throughout the humidification and sterilization cycles. Next, a vacuum may be drawn on the sterilization unit to achieve a vacuum of approximately 1.8 to 6.0 kPa. In a humidification cycle, steam then may be injected to provide a source of water vapor for the product to be sterilized. The packaged medical devices may be exposed to water vapor in the sterilization unit for a period of time of about 60 to 90 minutes. Times may vary, however, depending upon the medical device being sterilized.

Following this humidification portion of the cycle, the sterilization unit may be pressurized by the introduction of dry inert gas, such as nitrogen gas, to a pressure of between about 42 and 48 kPa. Once the desired pressure is reached, pure ethylene oxide may be introduced into the sterilization unit until the pressure reaches about 95 kPa. The ethylene oxide may be maintained for a period of time effective to sterilize the packaged medical device. For example, the ethylene oxide may be maintained in the sterilization unit for about 360 to about 600 minutes for surgical sutures. The time required to sterilize other medical devices may vary depending upon the type of product and the packaging. The ethylene oxide then may be evacuated from the sterilization unit and the unit may be maintained under vacuum at a pressure of approximately 0.07 kPa for approximately 150 to 300 minutes in order to remove residual moisture and ethylene oxide from the sterilized packaged medical devices. The pressure in the sterilization unit may be returned to atmospheric pressure.

The following stage of the process is a drying cycle. The packaged medical device may be dried by exposure to dry nitrogen and vacuum over a number of cycles sufficient to effectively remove residual moisture and water vapor from the packaged medical device to a preselected level. During these cycles, the packaged medical device may be subjected to a number of pressure increases and decreases, at temperatures greater than room temperature. Specifically, the jacket temperature of the drying chamber may be maintained at a temperature of between approximately 53° C. to 57° C. throughout the drying cycle. Higher temperatures, however, may be employed, such as about 65° C. to 70° C. for sutures, and higher depending upon the medical device being sterilized. A typical drying cycle includes the steps of increasing the pressure with nitrogen to approximately 100 kPa, evacuating the chamber to a pressure of approximately 0.07 kPa over a period of 180 to 240 minutes, reintroducing nitrogen to a pressure of 100 kPa and circulating the nitrogen for approximately 90 minutes, evacuating the chamber to a pressure of approximately 0.01 kPa over a period of approximately 240 to 360 minutes and maintaining a pressure of not more than 0.005 kPa for an additional 4 to 96 hours. At the end of the humidification, sterilization and drying cycles, which takes typically about 24 hours, the vessel is returned to ambient pressure with dry nitrogen gas. Once drying to the preselected moisture level is complete, the packaged medical device may be removed from the drying chamber and stored in a humidity controlled storage area.

Upon completion of the sterilization process, the antimicrobial medical device, the package and/or the packaging component have thereon an amount of the antimicrobial agent effective to substantially inhibit colonization of bacteria on or adjacent the antimicrobial device, the package and/or the packaging component.

As indicated above, it has been shown that the shelf life of an antimicrobial medical device, such as a triclosan-containing suture, can be limited by increasing levels of triclosan that occur during normal and accelerated storage conditions. In some case, shelf life is limited to a period not to exceed two years, due to the impact of this phenomenon. The packaged antimicrobial medical devices disclosed herein utilize an adsorbent or absorbent material to improve shelf life over packaged antimicrobial sutures that do not utilize an adsorbent or absorbent material. In accordance with the methods disclosed herein, in one embodiment, the method of making a packaged antimicrobial device includes the step of coating the adsorbent or absorbent material on at least a portion of one surface of the inner package. In another embodiment, the adsorbent or absorbent material is provided by placing an adsorbent or absorbent substrate within the outer package. In still another embodiment, the adsorbent or absorbent substrate is formed by coating a substrate with an adsorbent or absorbent material. In a still further embodiment, the adsorbent or absorbent substrate is formed of an adsorbent or absorbent material. In a yet still further embodiment, the inner package comprises a universal envelope formed from a paperboard stock having at least one surface coated with an adsorbent or absorbent material.

Adsorbent or absorbent materials include bentonite, activated carbon, activated alumina, silica gel, zeolite, superabsorbant polymers, humectants, polymeric coatings, ground polymeric coatings, natural products, non-paper substrates, and clays, including kaolin. Clays, such as kaolin, have proven to be particularly effective.

In one embodiment, a method of increasing the shelf life of a packaged antimicrobial medical device is provided. The method includes the steps of providing an inner package having a source of antimicrobial agent, providing an adsorbent or absorbent material effective to adsorb a portion of the antimicrobial agent over time, positioning a medical device within the inner package, the medical device comprising one or more surfaces, covering the inner package with an outer package having an inner surface and subjecting the medical device, the inner package and the inner surface of the outer package to time, temperature and pressure conditions sufficient to transfer an effective amount of the antimicrobial agent from the antimicrobial agent source to the medical device and the inner package, thereby substantially inhibiting bacterial colonization on the medical device and the inner package. The packaged antimicrobial medical device exhibits improved shelf life over a packaged antimicrobial medical device without an adsorbent or absorbent material so provided.

All patents, test procedures, and other documents cited herein, including priority documents, are fully incorporated by reference to the extent such disclosure is not inconsistent and for all jurisdictions in which such incorporation is permitted.

While the illustrative embodiments disclosed herein have been described with particularity, it will be understood that various other modifications will be apparent to and can be readily made by those skilled in the art without departing from the spirit and scope of the disclosure. Accordingly, it is not intended that the scope of the claims appended hereto be limited to the examples and descriptions set forth herein but rather that the claims be construed as encompassing all the features of patentable novelty which reside herein, including all features which would be treated as equivalents thereof by those skilled in the art to which this disclosure pertains.

When numerical lower limits and numerical upper limits are listed herein, ranges from any lower limit to any upper limit are contemplated.

What is claimed:

1. A method of making a packaged antimicrobial medical device, comprising:
   providing a package having at least an inner surface and an outer surface;
   positioning at least one medical device within the package;
   providing a source of antimicrobial agent external to the package;
   subjecting the medical device, at least the inner surface of the package and the antimicrobial agent source to time, temperature, and pressure conditions sufficient to transfer an effective amount of the antimicrobial agent from the antimicrobial agent source to the medical device and the inner surface of the package, thereby substantially inhibiting bacterial colonization on the medical device and the inner package surface; and
   providing an adsorbent or absorbent material within the package,
   wherein an inner package comprises a containment compartment that includes a plurality of patches, each patch having at least a pair of reservoirs formed of a porous medical grade paper or a permeable polymeric film or a fabric having a matrix structure, and an outer cover, the outer cover having one surface coated with the adsorbent or absorbent material.

2. The method of making a packaged antimicrobial medical device according to claim 1, wherein the adsorbent or absorbent material is formed by coating a substrate with an adsorbent material.

3. The method of making a packaged antimicrobial medical device according to claim 1, wherein the medical device positioned within the inner package is substantially free of antimicrobial agent.

4. The method of making a packaged antimicrobial medical device according to claim 1, wherein the antimicrobial agent is selected from the group consisting of halogenated hydroxyl ethers, acyloxydiphenyl ethers, and combinations thereof.

5. The method of making a packaged antimicrobial medical device according to claim 1, wherein the effective amount of the antimicrobial agent transferred from the source of antimicrobial agent to the medical device and the inner package is transferred during an ethylene oxide sterilization process.

6. The method of making a packaged antimicrobial medical device according to claim 1, wherein the step of subjecting the medical device and the inner surface of the package to conditions sufficient to transfer an effective amount of the antimicrobial agent comprises the steps of:
   placing the package and the medical device therein in a sterilization unit;
   heating the sterilization unit to a first temperature;
   adjusting the pressure in the sterilization unit to a first pressure value;
   injecting steam into the sterilization unit to expose the package and the medical device to water vapor for a first period of time;
   adjusting the pressure within the sterilization unit to a second pressure value;
   introducing a chemical sterilization agent into the sterilization unit;
   maintaining the chemical sterilization agent in the sterilization unit for a second period of time to render a sufficient amount of microorganisms non-viable;
   removing residual moisture and chemical sterilization agent from the medical device; and
   drying the packaged antimicrobial medical device to a desired moisture level.

7. The method of making a packaged antimicrobial medical device according to claim 6, wherein the step of introducing a chemical sterilization agent comprises introducing ethylene oxide gas into the sterilization unit.

8. The method of making a packaged antimicrobial medical device according to claim 1, wherein the medical device is selected from a suture, a surgical mesh, a hernia plug, a brachy seed spacer, a suture clip, a suture anchor, an adhesion prevention mesh or film or a suture knot clip.

9. The method of making a packaged antimicrobial medical device according to claim 1, wherein the package including the medical device is placed in a sealed environment and the antimicrobial agent source is contained in the sealed environment.

10. The method of making a packaged antimicrobial medical device according to claim 1, wherein the package including the medical device is placed in a sealed environment and the antimicrobial agent source is subsequently introduced into the sealed environment.

11. A method of making a packaged antimicrobial suture, the method comprising the steps of:
   providing an inner package having a source of antimicrobial agent, the source of antimicrobial agent comprising a plurality of patches, each patch having at least a pair of antimicrobial agent reservoirs;
   positioning at least one suture within the inner package, the at least one suture comprising one or more surfaces;
   covering the inner package with an outer package having an inner surface; and
   subjecting the at least one suture, the inner package, and the inner surface of the outer package to time, temperature, and pressure conditions sufficient to transfer an effective amount of the antimicrobial agent from the antimicrobial agent source to the at least one suture and the inner package, thereby substantially inhibiting bacterial colonization on the at least one suture and the inner package,
   wherein said antimicrobial agent reservoirs are formed of a porous medical grade paper or a permeable polymeric film.

12. A method of making a packaged antimicrobial suture, the method comprising the steps of:
   providing an antimicrobial agent from an external source to an inner package the inner package comprising a containment compartment having a base member and a channel cover member, the base member including an outer periphery, and an outer cover positioned upon channel cover member and within the outer periphery, to at least partially enclose at least one suture within the inner package, the at least one suture comprising one or more surfaces;
   covering the inner package with an outer package having an inner surface; and
   subjecting the at least one suture, the inner package, and the inner surface of the outer package to time, temperature, and pressure conditions sufficient to transfer an effective amount of the antimicrobial agent from the antimicrobial agent source to the at least one suture and the inner package, thereby substantially inhibiting bacterial colonization on the at least one suture and the inner package.

13. The method of making a packaged antimicrobial suture according to claim 12, wherein the antimicrobial agent is selected from the group consisting of halogenated hydroxyl ethers, acyloxydiphenyl ethers, and combinations thereof.

14. The method of making a packaged antimicrobial suture according to claim 12, wherein the antimicrobial agent is selected from the group consisting of halogenated hydroxyl ethers, acyloxydiphenyl ethers, and combinations thereof.

* * * * *